United States Patent
Panten et al.

(10) Patent No.: US 6,998,378 B2
(45) Date of Patent: Feb. 14, 2006

(54) 5,7,7-TRIMETHYLOCTANNITRIL

(75) Inventors: Johannes Panten, Luechtringen (DE); Karl-Georg Fahlbusch, Hoexter (DE); Mathias Werner, Hamburg (DE); Pascal Sillon, Hamburg (DE)

(73) Assignee: Symrise GmbH & Co. KG, Holzminden (DE)

( * ) Notice: Subject to any disclaimer, the term of this patent is extended or adjusted under 35 U.S.C. 154(b) by 97 days.

(21) Appl. No.: 10/684,726

(22) Filed: Oct. 14, 2003

(65) Prior Publication Data

US 2004/0127394 A1    Jul. 1, 2004

(30) Foreign Application Priority Data

Oct. 15, 2002   (DE) ............................... 102 47 966

(51) Int. Cl.
*C11D 3/395*   (2006.01)
*A61K 7/46*   (2006.01)
*C07C 255/02*   (2006.01)

(52) U.S. Cl. .................. 510/302; 512/6; 558/435; 424/400; 424/401

(58) Field of Classification Search ............... 558/435; 512/6; 424/400, 401; 510/302
See application file for complete search history.

(56) References Cited

U.S. PATENT DOCUMENTS 4,640,787 A    2/1987    Schuettenberg

FOREIGN PATENT DOCUMENTS

| EP | 0 017 396 A1 | 10/1980 |
|---|---|---|
| EP | 0 074 253 B1 | 6/1986 |
| EP | 0 347 596 A2 | 12/1989 |
| GB | 1 523 028 | 8/1978 |
| WO | WO 02/081614 A1 | 10/2002 |

OTHER PUBLICATIONS

Gutman et al., Synthesis and reactions of branched-chain hydrocarbons. I. Hydrocarbons with the 3,5,5-trimethylhexyl groups, Journal of the Chemical Society, Abstracts (1951) pp. 2064-2067.*

Bures et al., Thermochemical parameters of nitriles in the ideal gas state, Chemicky Prumysl (1990), 40(11-12), pp. 589-595.*

Pyryalova et al., Reduction of aromatic and branched-chain aliphatic nitriles by SnC12 (Stephen aldehyde Synthesis), Izvestiya Vysshikh Uchebnykh Zavedenii, Khimiya i Khimicheskaya Tekhnologiya (1965), 8(1), pp. 82-87.*

* cited by examiner

*Primary Examiner*—Johann Richter
*Assistant Examiner*—Ebenezer Sackey
(74) *Attorney, Agent, or Firm*—Pendorf & Cutliff

(57) ABSTRACT

The novel substance 5,7,7-trimethyloctanenitrile and certain uses of this substance, in particular as a fragrance, are described.

8 Claims, No Drawings

5,7,7-TRIMETHYLOCTANNITRIL

FIELD OF THE INVENTION

The present invention relates to 5,7,7-trimethyloctanenitrile, certain products containing a proportion of said substance (in particular fragrance compositions, perfumed articles and bleach compositions) and certain uses of the substance.

BACKGROUND OF THE INVENTION

Despite a multiplicity of already available fragrances, there continues to be a general need in the perfume industry for new fragrances which, in addition to their primary, specific odour, properties, have additional positive secondary properties such as, for example a higher stability under certain application conditions, improved spreading capacity, a better adhesion or the like.

It has already been known for a long time that the chemical group of substances comprising the nitrites contains a number of interesting fragrances. Known commercial products are citronellyl cyanide, geranyl cyanide and cinnamyl cyanide. A review of nitrites as fragrances is given by Vasanti G. Yadav in Perfumery Nitriles and Acetals: Part II, Synthesis and Characteristics of Nitriles, PAFAI J. (1994), 16 (2), 29–42. More recent publications on nitrites as constituents of perfumes are the patent documents U.S. Pat. No. 5,179,222, U.S. Pat. No. 6,180,814 and U.S. Pat. No. 5,521,151. The latter documents relate to nitrites, which, in addition to their primary odour characteristic, are characterized by a particularly high stability in aggressive media (for example aqueous solutions having a particularly high or particularly low pH value).

SUMMARY OF THE INVENTION

The primary aim of the present invention was to indicate a chemical compound, which can be used as a fragrance with a pronounced iris note and also has a high stability in aggressive media.

According to the invention, this aim is achieved by indicating the compound 5,7,7-trimethyloctanenitrile. In the context of the present text, the term 5,7,7-trimethyloctanenitrile includes the R-configured enantiomers, the S-configured enantiomers and (in particular racemic) mixtures of the enantiomers.

DETAILED DESCRIPTION

The structural formula of 5,7,7-trimethyloctanenitrile is given below:

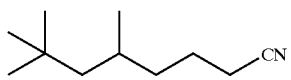

The odour characteristics of 5,7,7-trimethyloctanenitrile are described as: iris, vetiver, iris butter, woody, rooty.

In addition to its excellent odour characteristics, the substance also has an excellent stability in aggressive media, in which context bleach systems (bleaching agents) may be mentioned here in particular.

Surprisingly, it has been found that in respect of its properties, the invention (sic) according to the invention 5,7,7-trimethyloctanenitrile is even superior to the compound 2-nonenenitrile $CH_2(CH_2)CH=CH—CN$ which is also known by the name "iris nitrile". This is because 2-nonenenitrile has an odour strength that is undesired in perfumery, which makes it such a penetrating fragrance that it is justifiably stated in Arctander S., "Perfume and Flavour Chemicals", Vol. I, 1969, No. 2362, that the main difficulty in promoting this substance as a fragrance lies in its enormous (odour) strength. 5,7,7-trimethyloctanenitrile according to the invention is, in contrast, less penetrating and also differs from 2-nonenenitrile in respect of the odiferous secondary aspects, which are particularly appreciated by perfumerers.

As supplementary information, it is pointed out that in the tabular review of the odour characteristics of synthetic nitrites, which contains 48 substances, that is given by Yadav loc. cit., there is only one, specifically the compound 3-methyl-2-nonenenitrile (compound 13), that is designated as a fragrance having an iris note.

Whilst nitrites frequently have an odour that corresponds to that of the corresponding aldehydes (again cf. Yadav loc. cit.), there is no such odour relationship between 5,7,7-trimethyloctanenitrile according to the invention and its corresponding aldehyde. Thus, there is an odour deviation between nitrile and aldehyde, which Yadav would have termed an "anomalous odour effect".

The present invention also relates to fragrance compositions and to perfumed articles that contain an amount of 5,7,7-trimethyloctanenitrile that is effective from the sensory standpoint. Perfumerers who have worked on the use of the substance according to the invention have found that this has an (even) better performance than iris nitrile as a fragrance since, compared with iris nitrile, it produces more performance when used in a smaller amount.

The amount of 5,7,7-trimethyloctanenitrile in a fragrance composition according to the invention is preferably sufficient to modify and/or to intensify the fragrance composition in the iris direction.

According to the invention, a fragrance composition with an iris note is prepared by mixing 5,7,7-trimethyloctanenitrile with conventional further constituents of a fragrance composition, the 5,7,7-trimethyloctanenitrile being used in an amount that is sufficient to modify and/or to intensify the odour of the fragrance composition in the iris direction.

The use of the substance according to the invention in a bleaching agent composition is particularly preferred. Accordingly, a bleaching agent composition according to the invention contains a bleaching agent, 5,7,7-trimethyloctanenitrile and, optionally, conventional additives, the 5,7,7-trimethyloctanenitrile being present in an amount that is sufficient to modify and/or to intensify the odour of the bleaching agent composition in the iris direction. In this context, it is preferred that the bleaching agent comprises chlorine and/or hypochlorite.

Further preferred aspects and sub-aspects of the invention result from the following examples and the appended patent claims:

EXAMPLES

Perfume Compositions:
Example of the use of 5,7,7-trimethyloctanenitrile:

| | |
|---|---:|
| Aldehyde C-10 1% DPG | 8.00 |
| Aldehyde C-11 Lenic 1% DPG | 6.00 |
| Aldehyde C-9 10% DPG | 4.00 |
| Benzyl acetate | 65.00 |
| Brahmanol [1] | 10.00 |
| Cinnamic alcohol | 20.00 |
| Citronellol inactive | 90.00 |
| Citronellyl acetate | 40.00 |
| Clary sage oil Russia 10% DPG | 6.00 |
| DPG (dipropylene glycol) | 132.00 |
| Dupical [2] 10% DPG | 3.00 |
| Exaltolide Total [3] | 2.00 |
| Hedione [4] | 8.00 |
| Hexenyl acetate cis-3 10% DPG | 8.00 |
| Hexylcinnamic aldehyde | 160.00 |
| Indole 10% DPG | 15.00 |
| Indolene 50 [5] | 10.00 |
| Lemon Oil Italian SFUmatrice | 2.00 |
| Lilial [6] | 20.00 |
| Linalool synth. | 90.00 |
| Lyral [7] | 50.00 |
| Phenylethyl acetate | 25.00 |
| Phenylethyl alcohol | 140.00 |
| Phenylethyl isobutyrate | 5.00 |
| Rose oxide l 1% DPG | 6.00 |
| Sandalwood oil East India | 5.00 |
| Terpineol pure | 60.00 |
| 5,7,7-Trimethyloctanenitrile | 10.00 |
| | 1000.00 |

[1] Trade name owned by Dragoco, Holzminden, D
[2] Trade name owned by Quest, Ashford, GB
[3], [4] Trade name owned by Firmenich, Geneva, CH
[5], [6] Trade name owned by Givaudan, Zürich, CH
[7] Trade name owned by IFF, New Jersey, US Description of the odour: flowery, lily of the valley, very natural, very soft, iris.

Bleaching Agent Composition:

| | |
|---|---:|
| Sodium laurate (as 30% solution) | 1.5 |
| Coconut stearyldimethylamine oxide | 3.5 |
| Hypochlorite (as 13% solution) | 40.0 |
| Sodium hydroxide (as 30% solution) | 2.5 |
| Water | 52.4 |
| 5,7,7-Trimethyloctanenitrile | 0.1 |
| | 100.0 |

Preparation:

The preparation of 5,7,7-trimethyloctanenitrile is carried out in a manner known per se. Thus, Z/E-5,7,7-trimethyl-2(3)-octenenitrile which, surprisingly, from the odour standpoint is to be characterised completely differently to the compound according to the invention, cf. Yadov loc. cit., compound 8, can advantageously be prepared from isononyl aldehyde and cyanoacetic acid by means of a Knoevenagel reaction.

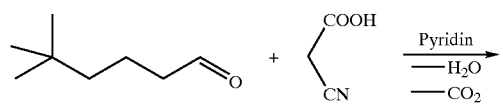

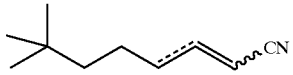

The subsequent hydrogenation to give the saturated

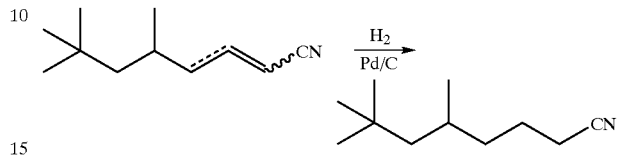

nitrile is then advantageously carried out using Pd/C:

Method of Preparation:

Step 1: Preparation of E/Z-5,7,7-trimethyl-2(3)-octenenitrile 300 g Toluene, 255 g (3 mol) cyanoacetic acid and 426 g (3 mol) isononyl aldehyde are initially introduced in the indicated order and the mixture is heated to 55–60° C. with stirring. 64 g Pyridine is then added dropwise in the course of 15 minutes without further heating. The temperature rises to 65° C. The mixture is then heated to the boil in the course of 45 min, and the water of reaction is separated off for 4 h in a water separator. The reaction mixture is cooled to 70–75° C. and washed at 70° C. with 2×150 g water, 2×150 g 10% $H_2SO_4$ and 1×150 g NaCl solution. It is then distilled.

Yield of E/Z-5,7,7-trimethyl-2(3)-octenenitrile (4 isomers): 270.7 g (55%)

Step 2: Hydrogenation to Give 5,7,7-trimethyloctanenitrile 270 g (1.6 mol) E/Z-5,7,7-trimethyl-2(3)-octenenitrile, 1.8 l ethanol and 3.24 g Pd/C are stirred for 10 h at 30° C. and 40 bar under hydrogen. GC is used to check that the hydrogenation has gone to completion.

The solvent is then stripped off and fractionation is carried out on a 20 cm GFCC.

Yield: 210.1 g (77%).

Spectroscopic Data:

5,7,7-Trimethyloctanenitrile:

$^1$H-NMR (CDCl$_3$, 300 MHz, TMS=0 ppm): δ=0.90 (s, 9H); 0.93 (d, 3H, J=6.5 Hz); 1.08 (dd, 1H, J=14.0 and 6.2 Hz); 1.21 (dd, J=14,0 and 3.5 Hz, 1H); 1.25–1.55 (m, 3H); 1.55–1.72 (m, 2H); 2.32 (t, 2H, J=7, 14 Hz).

$^{13}$C-NMR (CDCl$_3$, 75 MHz): δ=17.4 (t); 22.4 (q); 23.2 (t); 28.7 (d); 30.0 (3 q); 31.0 (s); 38.4 (t); 51.0 (t) 119.8 (s).

MS (m/e, %): 166 (M$^+$,0); 152 (58); 110 (13); 96 (23); 69 (13); 57 (100); 56 (11); 55 (13); 41 (26).

Precursor E/Z-5,7,7-trimethyl-2(3)-octenenitrile:

MS (m/e, %):

Isomer 1: 165 (M, 0); 150 (60); 108 (20); 94 (23); 67 (40); 57 (100); 41 (38).

Isomer 2: 165 (M, 1); 150 (20); 109 (25); 94 (50); 71 (40); 57 (100); 41 (30).

Isomer 3: 165 (M, 0); 150 (20); 123 (20); 108 (20); 99 (25); 67 (30); 57 (100); 41 (30).

Isomer 4: 165 (M, 15); 150 (20); 109 (40); 94 (15); 71 (20); 57 (100); 41 (40).

IR:

Isomer 1: ν (cm$^{-1}$)=2963.21; 2915.05; 1472.96; 1371.26; 1241.54.

Isomer 2: ν (cm$^{-1}$)=2964.67; 2914.47; 1471.77; 1371.36.
Isomer 3: ν (cm$^{-1}$)=2963.98; 2918.76; 2228.71; 1634.35; 1473.54; 1371.04; 966.55.
Isomer 4: ν (cm$^{-1}$)=2964.57; 2916.06; 1472.04; 1370.03; 971.37.

What is claimed is:

1. 5,7,7-trimethyloctanenitrile.

2. A fragrance composition or perfumed article comprising 5,7,7-trimethyloctanenitrile.

3. The fragrance composition or perfumed article according to claim 2, comprising a sufficient amount of 5,7,7-trimethyloctanenitrile for at least one of modifying or intensifying the fragrance composition in an iris direction.

4. A fragrance composition according to claim 2 wherein the 5,7,7-trimethyloctanenitrile is present in the composition in an effective amount from the sensory standpoint.

5. A method for preparing a fragrance composition having an iris note, the method having the steps of:
   mixing 5,7,7-trimethyloctanenitrile with a fragrance composition, the 5,7,7-trimethyloctanenitrile being used in a sufficient amount for at least one of modifying or intensifying the odour of the fragrance composition in an iris direction.

6. A bleaching agent composition comprising:
   a bleaching agent;
   5,7,7-trimethyloctanenitrile; and
   optionally at least one additive,
   wherein the 5,7,7-trimethyloctanenitrile is present in a sufficient amount for at least one of modifying or intensifying the odor of the bleaching agent composition in the iris direction.

7. Bleaching agent composition according to claim 6 wherein the bleaching agent comprises at least one of chlorine or hypochlorite.

8. The compound of claim 1, wherein the compound is prepared by:
   a) reacting isononyl aldehyde with cyanoacetic acid; and
   b) reacting the product of step a) with hydrogen.

* * * * *